United States Patent [19]

Turner

[11] Patent Number: 5,226,592
[45] Date of Patent: Jul. 13, 1993

[54] RADIATOR HEAT DISTRIBUTING APPARATUS

[76] Inventor: Terrence E. Turner, 11423 S. Hermosa, Chicago, Ill. 60643

[21] Appl. No.: 881,176

[22] Filed: May 11, 1992

[51] Int. Cl.⁵ .................................................. F24F 7/00
[52] U.S. Cl. ...................................... 236/49.3; 237/79
[58] Field of Search .................... 237/78 R, 79, 53, 70, 237/71; 165/122, 54; 236/36, 38, 40, 49.3

[56] References Cited

U.S. PATENT DOCUMENTS 1,914,812  6/1933  Kresser ............................ 237/78 X
3,151,671 10/1964  Kritzer ............................. 237/79 X Primary Examiner—Henry A. Bennet
Attorney, Agent, or Firm—Leon Gilden

[57] ABSTRACT

A housing member is arranged for mounting above and receiving an associated radiator assembly. The housing member includes spaced end walls, with each end wall including a fan member having a thermostatically operative fan to direct and project heat from interiorly of the housing. A modification of the invention includes scent distribution structure mounted adjacent the fan members in coaxially aligned relationships thereto.

3 Claims, 4 Drawing Sheets

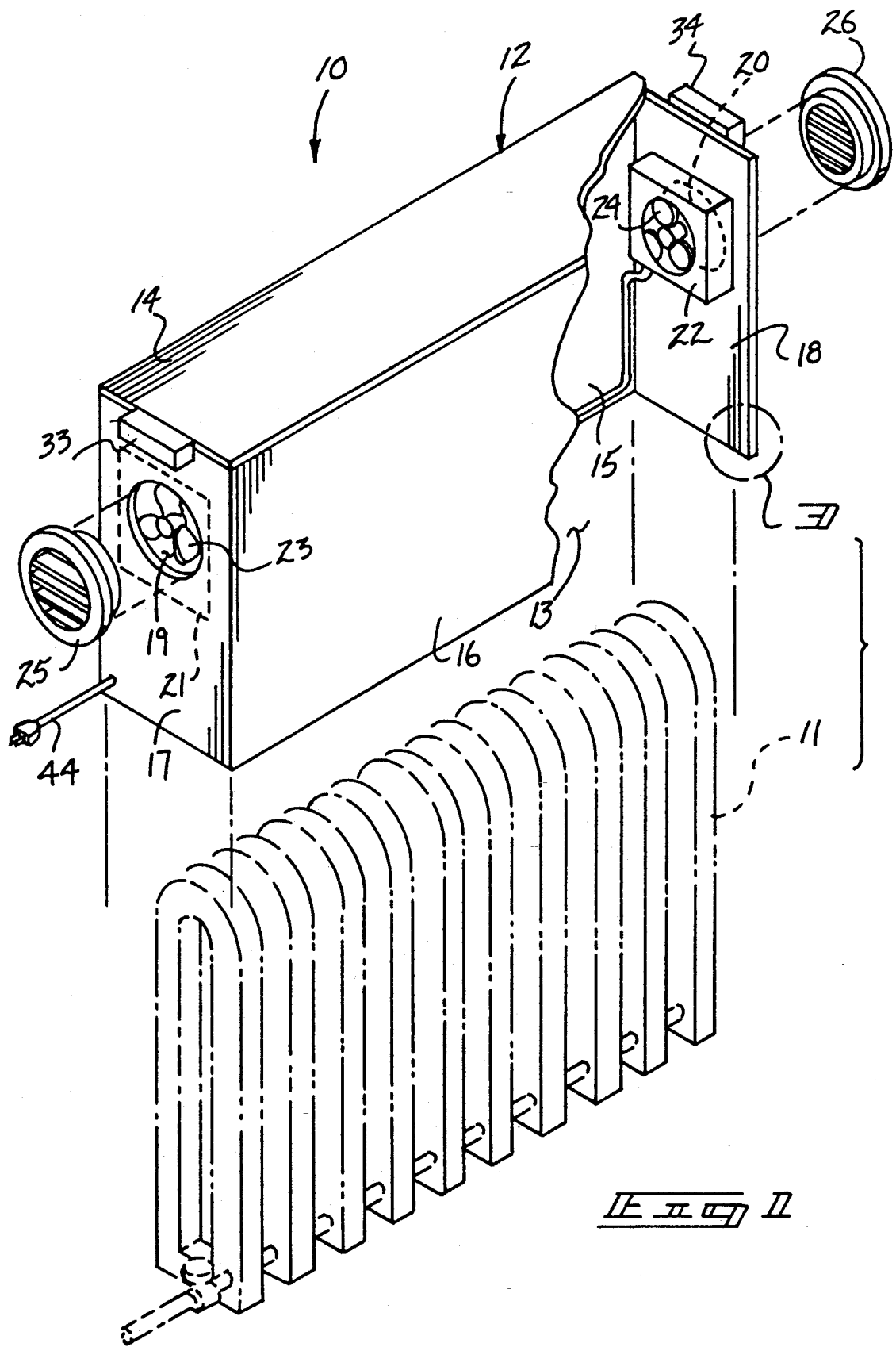

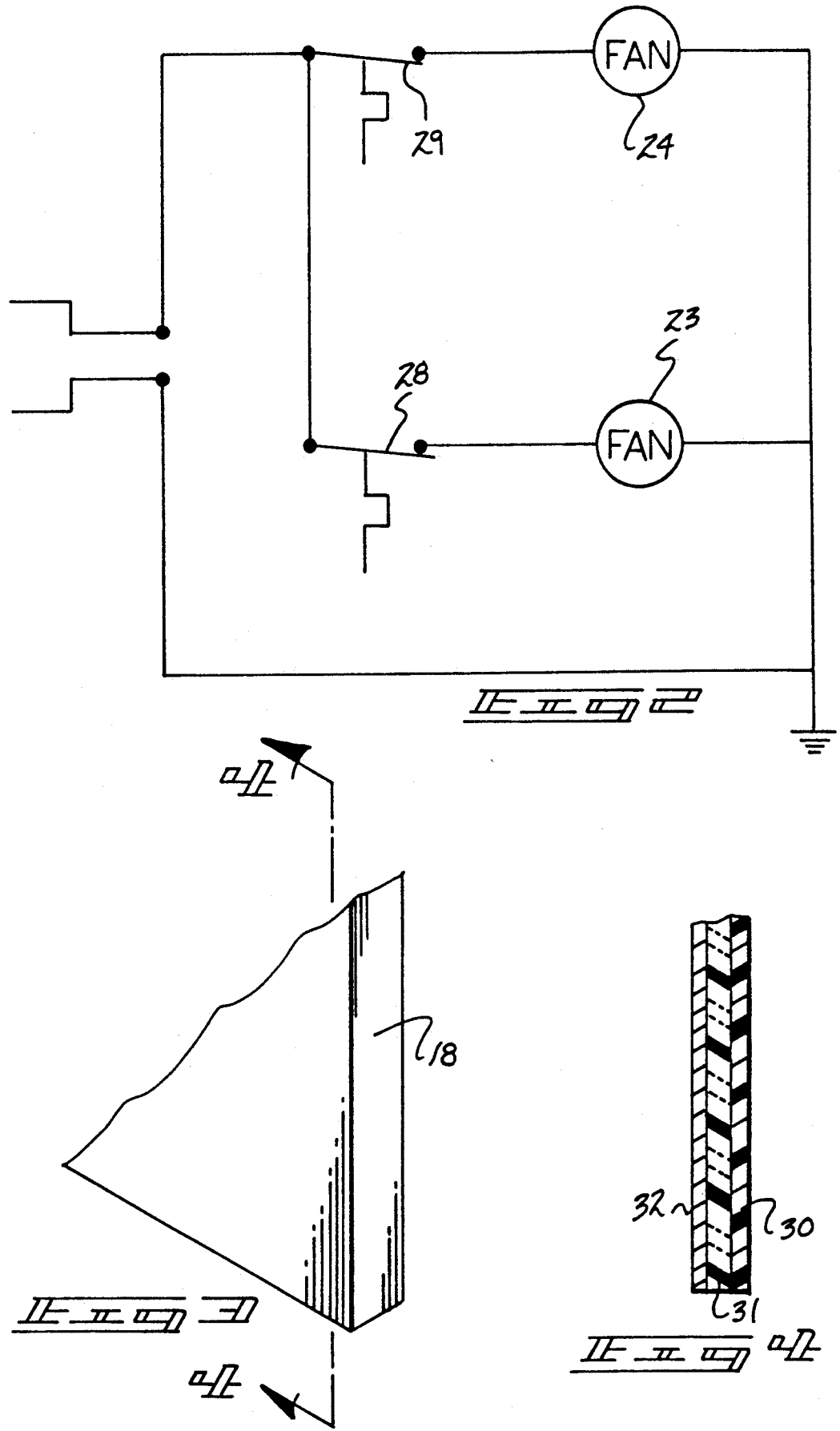

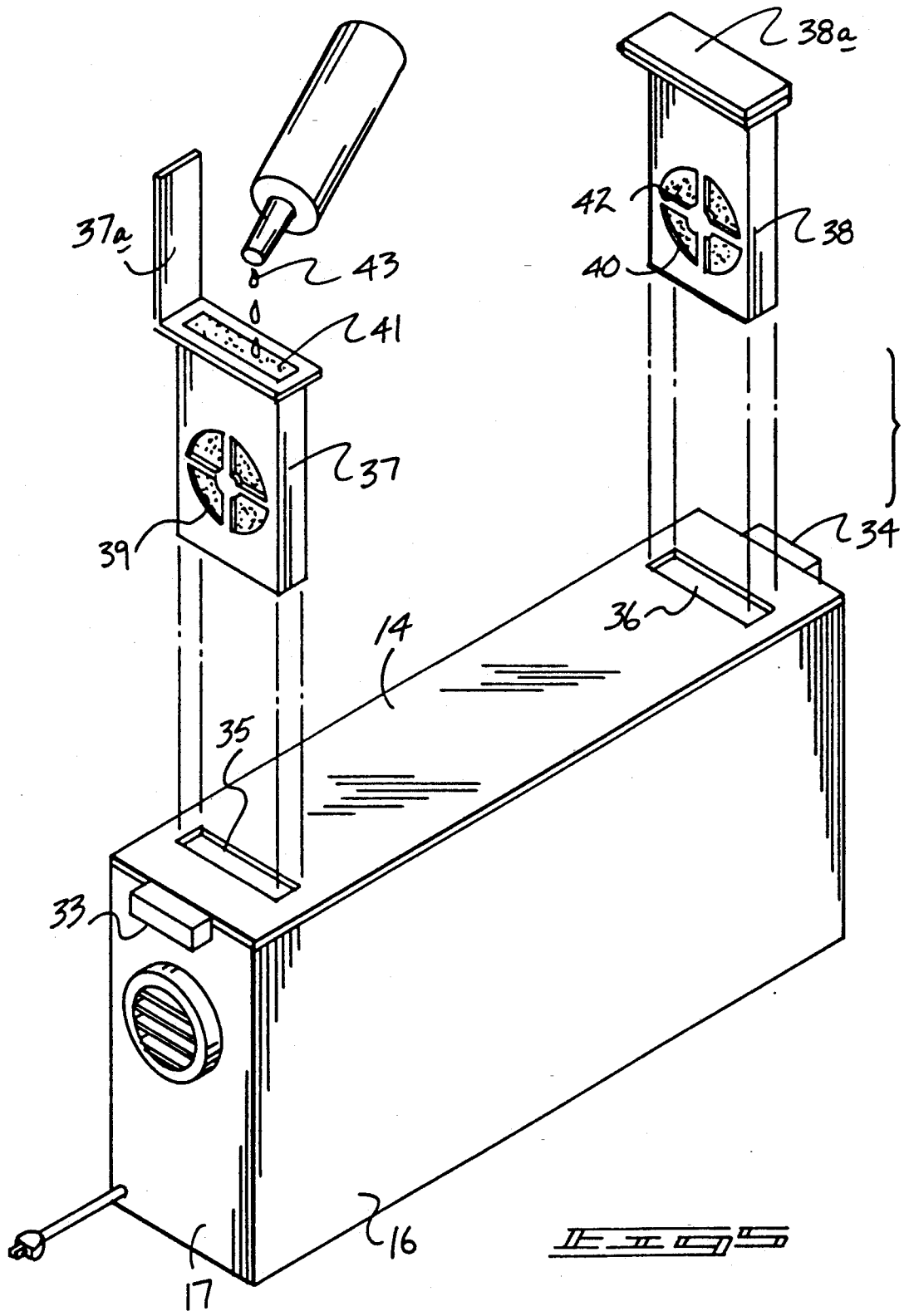

RADIATOR HEAT DISTRIBUTING APPARATUS

BACKGROUND OF THE INVENTION

1. Field of the Invention

The field of invention relates to heating apparatus, and more particularly pertains to a new and improved radiator heat distributing apparatus wherein the same is directed to the distribution of heat relative to a radiator member.

2. Description of the Prior Art

Radiant heat is typically directed from a conventional radiator assembly and typically requires a time delay to heat an associated environment. The instant invention attempts to overcome deficiencies of the prior art by providing for a heat distribution structure receiving an associated radiator therewithin. Prior art structure relative to the distribution of heat and the like are set forth in the U.S. Pat. Nos. 4,823,768; 4,768,212; 4,856,581; 4,705,097; and 4,841,557.

Accordingly, it may be appreciated that there continues to be a need for a new and improved radiator heat distributing apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of heating apparatus now present in the prior art, the present invention provides a radiator heat distributing apparatus wherein the same is arranged for forcibly directing heat from an associated radiator relative to a surrounding environment to the radiator structure. As such, the general purpose of the present invention, which will be described subsequently in greater detail, is to provide a new and improved radiator heat distributing apparatus which has all the advantages of the prior art heating apparatus and none of the disadvantages.

To attain this, the present invention provides a housing member arranged for mounting above and receiving an associated radiator assembly. The housing member includes spaced end walls, with each end wall including a fan member having a thermostatically operative fan to direct and project heat from interiorly of the housing. A modification of the invention includes scent distribution structure mounted adjacent the fan members in coaxially aligned relationships thereto.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved radiator heat distributing apparatus which has all the advantages of the prior art heating apparatus and none of the disadvantages.

It is another object of the present invention to provide a new and improved radiator heat distributing apparatus which may be easily and efficiently manufactured and marketed.

It is a further object of the present invention to provide a new and improved radiator heat distributing apparatus which is of a durable and reliable construction.

An even further object of the present invention is to provide a new and improved radiator heat distributing apparatus which is susceptible of a low cost of manufacture with regard to both materials and labor, and which accordingly is then susceptible of low prices of sale to the consuming public, thereby making such radiator heat distributing apparatus economically available to the buying public.

Still yet another object of the present invention is to provide a new and improved radiator heat distributing apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the instant invention.

FIG. 2 is a diagrammatic illustration of the thermostatically controlled fan structure utilized by the invention.

FIG. 3 is an isometric illustration of section 3, as set forth in FIG. 1.

FIG. 4 is an orthographic view, taken along the lines 4—4 of FIG. 3 in the direction indicated by the arrows.

FIG. 5 is an isometric illustration of the invention incorporating scented housing members mounted within the central housing of the organization.

DESCRIPTION OF THE PREFERRED EMBODIMENT

Figure 6:
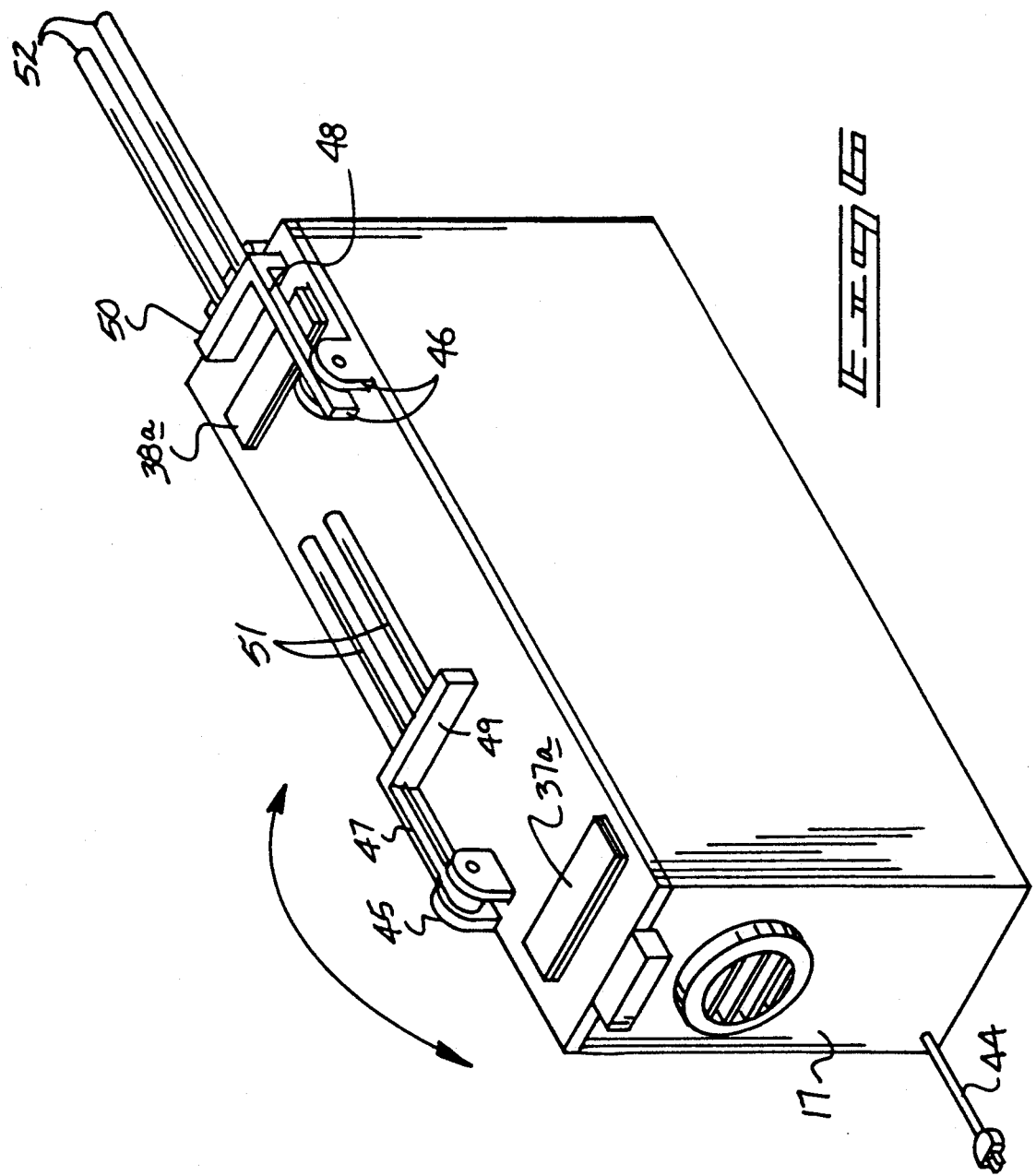
FIG. 6 is an isometric illustration of the invention utilizing drying posts pivotally mounted to the top wall of the structure housing.

With reference now to the drawings, and in particular to FIGS. 1 to 6 thereof, a new and improved radiator heat distributing apparatus embodying the principles and concepts of the present invention and generally designated by the reference numeral 10 will be described.

More specifically, the radiator heat distributing apparatus 10 of the instant invention essentially comprises a radiator assembly 11 received within a housing 12. The housing 12 includes a housing cavity 13 to receive the radiator assembly 11 therewithin. The housing includes a top wall 14, a first side wall 15 spaced from a second side wall 16, and a first end wall 17 spaced from a second end wall 18. The first end wall 17 and the second end wall 18 include respective first and second end wall openings 19 and 20, with a first fan housing 21 and a second fan housing 22 coaxially aligned relative to the respective first and second end wall openings 19 and 20. A first fan member 23 is mounted within the first fan housing 21 coaxially aligned with the first end wall opening 19 and a second fan member 24 mounted within the second fan housing 22 coaxially aligned with the second end wall opening 20. Respective first and second rotary defuser panels 25 and 26 are rotatably mounted within the first and second end wall openings 19 and 20 having spaced parallel louvers to selectively direct air about a surrounding environment relative to the radiator assembly 11. Electrical power supply 27 typically includes a heat shielded covering thereabout and directed into the fan housing cavity to direct electrical energy to the respective first and second fan members 23 and 24 that in turn include respective first and second thermal switches 28 and 29 preset at predetermined temperatures to effect automatic actuation of the fan members.

The wall structure of the housing, as exemplified in the FIG. 4, is formed with an outer polymeric layer 30 having an insulative central core 31 coextensive with the outer layer 30 and a heat conductive metallic inner layer 32 coextensive with the wall structure. First and second handles 33 and 34 are mounted to the first and second end walls adjacent the top wall for ease of manipulation of the housing 12 for manipulating the housing 12 relative to the associated radiator assembly 11.

The FIG. 5 illustrates the use of respective top wall first and second slots 35 and 36 positioned in a parallel relationship relative to the respective first and second end walls 15 and 16 receiving respective first and second sponge housings 37 and 38 that are arranged in a parallel relationship relative to and adjacent the fan housings 23 and 24 respectively. The first and second sponge housings 37 and 38 have first and second respective lids 37a and 38a to direct a deodorizing fluid 43 into an associated first and second sponge core 41 and 42 positioned coextensively within the first and second sponge housings 37 and 38. The housings 37 and 38 include respective first and second sponge housings openings 39 and 40 that are coaxially aligned with the respective first and second fan members 23 and 24 to direct a deodorizing scented mixture into the air directed exteriorly of the first and second end walls.

FIG. 6 further includes the top wall 14 having respective first and second support flanges 45 and 46 that pivotally mount respective first and second support arms 47 and 48 at lower distal ends of the first and second support arms that in turn are orthogonally oriented relative to the respective first and second end walls 17 and 18. The first and second support arms 47 and 48 orthogonally mount first and second mounting plates 49 and 50 at outer distal ends of the first and second support arms spaced from the support flanges, with the first and second mounting plates 49 and 50 having first and second mounting rods 51 and 52 arranged in a parallel relationship relative to one another and orthogonally oriented relative to the first and second mounting plates 49 and 50. In this manner, various articles of clothing may be positioned forwardly of the respective first and second end walls to permit drying of various garments and the like about the housing structure 12.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A radiator heat distributing apparatus, comprising.
   a housing arranged for reception of a radiator assembly therewithin, the housing having a top wall, a first side wall spaced from a second side wall, a first end wall spaced from a second end wall having an entrance positioned below the top wall defining a housing cavity within the housing between the top wall, first side wall, second side wall, first end wall, and the second end wall, and
   the first end wall including a first end wall opening, the second end wall including a second end wall opening, and
   a first fan housing mounted within the housing cavity adjacent the first end wall opening, a second fan housing mounted within the housing cavity adjacent the second end wall opening, and
   the first fan housing including a first fan member coaxially aligned with the first end wall opening, the second fan housing including a second fan member mounted within the second fan housing coaxially aligned with the second end wall opening, and control means for effecting selective actuation of the first fan member and the second fan member simultaneously upon temperature of the radiator assembly attaining a predetermined temperature, and a first rotary defuser panel mounted within the first end wall opening, and a second rotary defuser panel mounted rotatably within the second end wall opening, and each wall of said first end wall, second end wall, first side wall, second side wall, and top wall include an outer polymeric layer, an insulative central core, and a heat conductive metallic inner layer.

2. An apparatus as set forth in claim 1 including a top wall first slot directed through the top wall adjacent the first end wall, and a second top wall slot directed through the top wall adjacent the second end wall, and a first sponge housing slidably received through the first slot parallel to the first end wall adjacent the first fan housing, and a second sponge housing directed through the second slot parallel the second end wall and adjacent the second fan housing, the first sponge housing including a first sponge housing opening coaxially aligned with the first end wall opening, the second sponge housing including a second sponge housing opening coaxially aligned with the second end wall opening, the first sponge housing including a first sponge member within the first sponge housing having a deodorizing fluid directed therethrough, the second sponge member within the second sponge housing having further deodorizing fluid directed therethrough.

3. An apparatus as set forth in claim 2 including a first support arm pivotally mounted to the top wall orthogonally oriented relative to the first end wall, a second support arm pivotally mounted to the top wall orthogonally oriented relative to the second end wall, the first support arm having a first mounting plate fixedly and orthogonally mounted to an outer distal end of the support arm, a second mounting plate fixedly and orthogonally mounted to the second support arm at an outer distal end of the second support arm, and the first mounting plate including a plurality of first mounting rods orthogonally oriented to the first mounting plate projecting beyond the first end wall when the first support arm is pivoted in the second position projecting the first mounting rods beyond the first end wall from a first position positioning the first mounting rods over the top wall, the second mounting plate including a plurality of second mounting rods orthogonally oriented to the second mounting plate projecting orthogonally beyond the second end wall in the second position projecting the mounting rods beyond the second end wall in an orthogonal relationship from said first position positioning the second mounting rods over the top wall.

* * * * *